United States Patent [19]

Pace

[11] 4,454,007
[45] Jun. 12, 1984

[54] ION-SELECTIVE LAYERED SENSOR AND METHODS OF MAKING AND USING THE SAME

[75] Inventor: Salvatore J. Pace, Wilmington, Del.

[73] Assignee: E. I. Du Pont de Nemours and Company, Wilmington, Del.

[21] Appl. No.: 461,479

[22] Filed: Jan. 27, 1983

[51] Int. Cl.³ .................................... G01N 27/46
[52] U.S. Cl. .................................. 204/1 T; 204/416; 204/418; 204/403; 204/435; 427/96; 427/122
[58] Field of Search .............. 204/416, 418, 403, 435, 204/1 T; 427/96, 122

[56] References Cited

U.S. PATENT DOCUMENTS

| | | | |
|---|---|---|---|
| 4,020,830 | 5/1977 | Johnson et al. | 128/2 |
| 4,053,381 | 10/1977 | Hamblen et al. | 204/195 |
| 4,133,735 | 1/1979 | Afromowitz et al. | 204/195 |
| 4,184,936 | 1/1980 | Paul et al. | 204/416 X |
| 4,214,968 | 7/1980 | Battaglia et al. | 204/195 |
| 4,225,410 | 9/1980 | Pace | 204/195 |
| 4,272,328 | 6/1981 | Kim et al. | 204/418 X |
| 4,273,639 | 6/1981 | Gottermeier | 204/416 |
| 4,276,141 | 6/1981 | Hawkins | 204/195 |

FOREIGN PATENT DOCUMENTS 56-157851 12/1981 Japan .................................. 204/416

OTHER PUBLICATIONS

Schindler et al., "Potassium-Sel. Disc Electrode with Valinomycin for Flow-Through Measurements", Biomedizimsche Technik, vol. 21, No. 5, pp. 135-137, 6/1976.

Primary Examiner—G. L. Kaplan
Assistant Examiner—Nam X. Nguyen

[57] ABSTRACT

A layered half cell comprising (a) an inert insulating substrate having coated thereon (b) a layer of conductive material having coated thereon (c) a layer of carbon dispersed in a dielectric polymer, the layer being coated with (d) an ion-selective membrane layer, the interface between layers (c) and (d) being partially interdiffused.

22 Claims, 3 Drawing Figures

ION-SELECTIVE LAYERED SENSOR AND METHODS OF MAKING AND USING THE SAME

FIELD OF THE INVENTION

The invention is directed to an electrochemical sensor and, in particular, to an ion-selective layered half cell which is useful for clinical applications.

BACKGROUND OF THE INVENTION

Electrochemical devices are used extensively in clinical applications to detect electrical activity in living systems as in the case of the electrocardiogram (ECG) and the electroencephalogram (EEG). They are also widely used in the clinical analysis of biological fluids.

Electrochemical sensors can be devised to sense a wide range of species of interest (analyte) including electrolytes, blood gases, metabolites, drugs and hormones. This, together with the relative ease of their fabrication and use, makes them ideally suited to health care applications. They are, for example, sensitive, selective, compatible with whole blood samples, require relatively small sample sizes and are less prone to interferences, than other commonly used methods. The small size of such devices, the fact that few, if any, external reagents are required and the relatively simple instrumentation involved makes them desirable for use in emergency, critical care and surgical settings.

Other applications of electrochemical sensors include personal dosimetry for monitoring occupational exposure to toxic substances, chemical process monitoring and control, microbial process monitoring and the control of prosthetic devices.

There is a need for improved electrochemical sensors which are dependable, versatile, stable on standing and in storage and inexpensive to manufacture so that many of the traditional disadvantages of such sensors (i.e., poisoning, drifts and offsets) can be minimized or even eliminated by disposing of the device after a single use.

BRIEF SUMMARY OF THE INVENTION

The invention is therefore directed primarily to a layered half cell comprising:

(a) a dimensionally stable chemically inert electrically insulating substrate layer having coated thereon (b) a terminated layer of electroconductive material, the conductivity of which is at least $1 \times 10^2$ (ohms-cm)$^{-1}$ having coated thereon (c) a layer of finely divided particles of carbon uniformly dispersed in a matrix of organic polymeric binder having coated thereon (d) an ion-selective membrane layer comprising an ionophoric material uniformly dispersed in a matrix of dielectric organic polymer, the layer having an impedance at least two orders of magnitude greater than the impedance of the carbon layer, the interface between the ion-selective membrane layer and the carbon dispersion layer comprising a zone in which the layers are partially interdiffused. In use, layers (b) and (c) being shielded from both chemical and electroconductive contact with any analyte which may be present.

As used herein, the term "half cell" refers to an assemblage of interfaces at which ionic motion is converted to electron motion. A complete sensor is comprised of two such half cells which may also be referred to as electrodes, one of which is an indicator and the other a reference half cell.

In other aspects, the invention is directed to sensors which employ the layered half cells of the invention as sensing and reference electrodes and to the use of such sensors for measuring the relative concentrations of selected ions contained in a liquid analyte.

BRIEF DESCRIPTION OF THE DRAWING

The drawing, which consists of two sheets, contains three figures.

PRIOR ART

Figure 1:
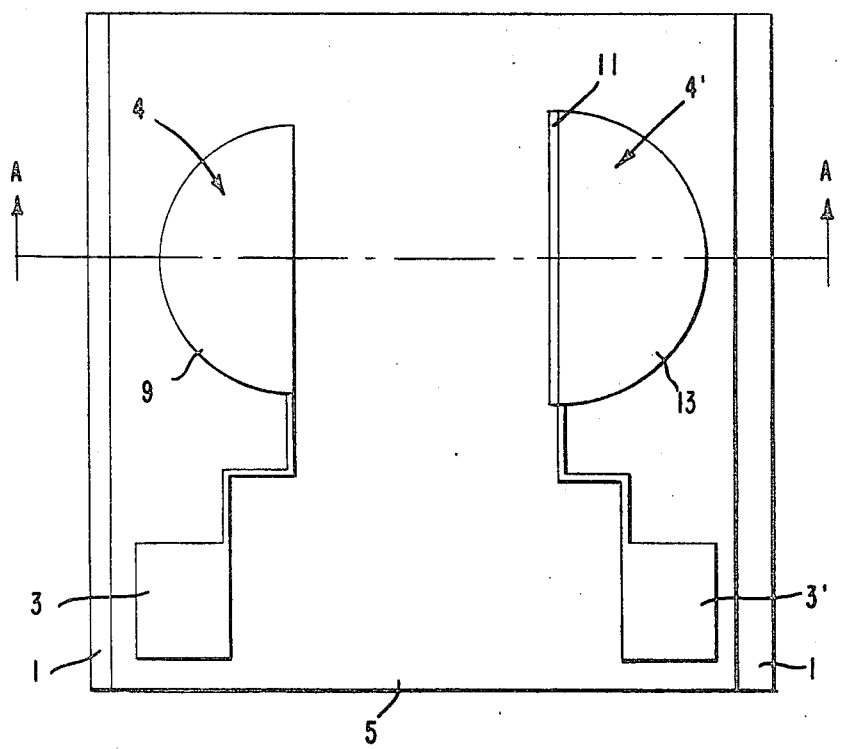
FIG. 1 is a schematic overhead view of a sensor incorporating two half cells of the invention and FIG. 2 is a schematic sectional view of the same sensor showing the various layers thereof taken along a section defined by the lines A—A.

Ion-selective electrode half cells are, of course, well known in the prior art, as is illustrated by the patents which are summarized below:

U.S. Pat. No. 4,020,830 Johnson et al.

This patent is directed to a field effect transistor (FET) transducer comprising an ion-selective membrane deposited over the gate region of the FET. When the "gate" is exposed to a test solution, the electrochemical potential modulates the gate voltage and thus the source-to-drain current.

U.S. Pat. No. 4,053,381, Hamblen et al.

This patent is directed to a layered electrode comprising an ion-selective membrane layer coated over an internal reference element supported on a substrate. The reference element can itself consist of several layers such as a metal layer in contact with a soluble salt layer which, in turn, is in contact with a layer of electrolyte dissolved in a solid hydrophilic binder such as polyvinyl alcohol, agarose or deionized gelatin.

U.S. Pat. No. 4,133,735, Aframowitz

The Aframowitz patent is directed to a layered ion-sensitive electrode comprising a planar substrate to which are bound separate first and second regions of conductive material. An ion-sensitive membrane is bonded to a substrate wafer and the first conductor region and the electrical output means are connected to the second conductor region. The wafer, the second conductor region and the output means are encapsulated to make them fluid-tight.

U.S. Pat. No. 4,225,410 Pace

The Pace patent is directed primarily to an array of electrodes for analyzing different analytes supported on a common substrate. At least one of the layered electrodes is for the purpose of calibration and consists of a first electrode layer containing a given concentration of analyte and a second electrode layer containing a given but different concentration of analyte.

DETAILED DESCRIPTION OF THE INVENTION

A. Ion-Selective Membrane

Ion-selective membranes have been used extensively in liquid membrane electrodes, especially in recent years. These membranes basically are comprised of either an electrically charged or neutral ligand (ionophore) dispersed in an inert matrix.

A wide variety of ionophoric materials is available for different ion selectivity such as those listed in Table 1 which follows:

TABLE I
IONOPHORIC MATERIALS FOR MEMBRANE ELECTRODES

| Analyte Ion | Ionophore |
|---|---|
| $K+$ | Valinomycin |
| | Crown ethers, e.g., dimethyldibenzo-30-crown-10, dicyclohexyl-18-crown, dimethyldicyclohexyl-18-crown-6. |
| $Na+$ | Methyl monensin, |
| $Ca^{2+}$ | Didecyl phosphoric acid + dioctyl phenyl phosphate |
| | Thenoyltrifluoroacetone + tributylphosphate |
| | Mono- and di-esters of phosphoric acid + di(2-ethylhexyl)2-ethylhexyl-phosphonate |
| | Calcium didecylphosphate + di-(octylphenyl) phosphonate |
| | Calcium di(octylphenyl) phosphate + dioctylphenyl-phosphonate |
| $Ba^{2+}$ | Calcium di-(2 ethylhexyl) phosphate + decan-1-ol |
| | Barium complex of nonyl-phenoxypoly (ethylene oxy) ethanol in o-nitro-diphenyl ether |
| $Cl^-$ | Ag/AgCl with halide scavenger Aliquat 336S in decan-1-ol shaken with aqueous solution of appropriate sodium salt |
| $HCO_3^-$ or total-$(CO_2)$ | Quaternary ammonium ion exchanger p-octodecyloxy-m-chlorophenyl-hydrazone-mesoxalonitrile (OCPH) |
| $NH_4+$ | Nonactin |
| | Monactin |
| $NO_3-$ | Tridodecylhexadecylammonium nitrate + n-octyl-o-nitrophenyl |
| | 1:10 phenanthroline nickel (II) nitrate + p-nitrocymene |
| $H+$ | Trioctylamine |

As is shown in Examples 26–32, the concentration of ionophore in the ion selective layer is not highly critical. Typically, from about 0.5% by weight of the layer can be used, with about 3.0% by weight ionophore being preferred to obtain maximum sensitivity for any given system. Still higher concentrations of ionophore can be used without any particular disadvantage, but no further benefit appears to be obtained. However, it is important that the ion carrying capacity of the ionophoric layer not be saturated. Therefore, it may be necessary to increase the ionophore level for analytes which have very high concentrations of the selected ions.

By far the most widely used membrane matrix materials are noncrystalline, hydrophobic polymers such as those listed in Table 2 below:

TABLE 2
HYDROPHOBIC POLYMERS FOR MEMBRANE ELECTRODE MATRICES

Poly(vinylchloride) [PVC]
Cellulose Acetate
Poly(bisphenol-A carbonate)
Polysiloxane/Poly(bisphenol-A carbonate) block copolymer
Poly(methylmethacrylate)
Poly(vinylidene chloride)
Polystyrene
Lower alkyl acrylate and methacrylate polymers and copolymers
Polyurethane
Silicone rubber The matrix polymer must be a chemically resistant, high dielectric material and preferably somewhat more conductive than an electrical insulator.

Of the foregoing listed polymers which are suitable for use as a membrane electrode matrix, PVC is by far the most widely used.

Generally, the matrix polymer is combined with a plasticizer to effect a certain amount of swelling of the polymer. This is in many instances necessary to allow for sufficient mobility of ion carriers through the membrane.

Among the plasticizers which have been used in this application are dioctyl adipate, tris(2-ethylhexyl) phosphate, dibutyl sebacate, o-nitrophenyl octyl ether, diphenyl ether, dinonyl phthalate, dipentyl phthalate, di-2-nitrophenyl ether, glycerol triacetate, tributyl phosphate, and dioctyl phenyl phosphate.

Ion-selective membranes of this type are usually made by forming a solution of the polymer and plasticizer (if one is used) in a volatile organic solvent, casting the solution onto the desired surface or into the desired shape and then removing the solvent by evaporation.

In addition to the above-mentioned criteria, the materials which constitute the ionophoric layer must be chosen so that the electrical impedance of that layer is at least two orders of magnitude and preferably at least five orders of magnitude higher than the electrical impedance of the underlying dispersed carbon layer. If the impedance is substantially less than this value, ion and-/or ionophore mobility is excessive for normal electrode operation. On the other hand, the impedance of the membrane layer must not be too high lest it approach the impedance of the electrometer and incur an impedance loading effect which will result in substantial errors of measurement. For this reason, it is preferred that the impedance of the ionophoric layer be at least about two orders of magnitude less than the impedance of the electrometer used to measure the potential between the conductive layer of the half cells of the invention.

B. Carbon Layer

The dispersed carbon layer consists essentially of a dispersion of finely divided particles of carbon in a matrix of dielectric organic hydrophobic polymer. The precise configuration of the carbon particles is not critical. For example, carbon black as well as finely divided pellets and charcoal particles can be used. However, it is essential that the amount of carbon be sufficient that the carbon polymer dispersion layer has an electrical impedance of less than about 1% of the impedance of the ion-selective membrane.

However, in view of the fact that the dispersed carbon layer must be partially diffused into the ion-selective membrane, it will be apparent that the carbon particles must be finely divided; that is, they must be substantially smaller than the thickness of either the membrane layer or the carbon layer. Depending on the thickness of the layer, which is not by itself critical, a particle size of from 1 to 20 μm is preferred, from 1 to 10 μm being particularly preferred.

The particular organic polymer used as matrix for the carbon particles is, likewise, not particularly critical so long as the polymer is a dielectric and forms a matrix which is nonreactive with both the carbon and the ion-selective membrane layer. For example, all of the polymers which are suitable for the matrix of the membrane layer are also suitable as the matrix for the dispersed carbon layer. In addition, more highly crystalline polymers such as polyethylene and polypropylene can be used.

Suitable matrix polymers for the dispersed carbon layer also include film-forming oleophilic polymers such as poly(caprolactone); polyacrylate and alpha-alkyl polyacrylate esters, e.g., polymethacrylate, polymethyl methacrylate and polyethyl methacrylate; vinylidene chloride copolymers, e.g., vinylidene chloride/acrylonitrile, vinylidene chloride/methacrylate and vinylidene chloride/vinylacetate copolymers, ethylene/-vinyl acetate copolymers; polyethylene; polyvinyl esters, e.g., polyvinyl acetate/acrylate, polyvinyl acetate/methacrylate and polyvinyl acetate; copolyesters, e.g., those prepared from the reaction product of a polymethylene glycol of the formula $HO(CH_2)_nOH$, wherein n is a whole number 2 to 10 inclusive, and (1) hexahydroterephthalic, sebacic and terephthalic acids, (2) terephthalic, isophthalic and sebacic acids, (3) terephthalic and sebacic acids, (4) terephthalic and isophthalic acids, and (5) mixtures of copolyesters prepared from said glycols and (i) terephthalic, isophthalic, sebacic and adipic acids; nylons or polyamides, e.g., N-methoxymethyl polyhexamethylene adipamide; synthetic rubbers, e.g., butadiene/acrylonitrile copolymers, and chloro-2-butadiene-1,3-polymers; block copolymers, e.g., polystyrene-polybutadiene-polystyrene and polystyrene-polyisoprene; poly(vinyl chloride) and copolymers, e.g., poly(vinyl chloride/acetate); polyvinyl acetal, e.g., poly(vinyl butyral), poly(vinyl formal) polyurethanes; polycarbonates; polystyrene; phenolic resins; and melamine-formaldehyde resins.

In some instances, plasticization of the matrix polymer for the dispersed carbon layer may not be needed. However, to minimize the formation of unwanted concentration gradients between the ion-selective membrane and the dispersed carbon layer, use of the same, or at least similar, polymers in the two layers is preferred. Thus, when PVC plasticized with dioctyl phthalate is used as the matrix for the membrane layer, a most convenient and economical way of minimizing migration of species between the layers is to use the same plasticized PVC composition as the matrix for the dispersed carbon layer. Furthermore, interdiffusion of the layers is facilitated by the mutual solubility of the matrices.

As will be made clear in the following discussion of the fabrication of the electrode half cells of the invention, it is preferred that the dispersed carbon layer matrix polymer be plasticized to some extent to facilitate interdiffusion of the membrane and carbon layers.

C. Salt Bridge Layer

When the layered half cell of the invention is used as a reference electrode instead of the primary sensing or indicating electrode, the ionophoric layer will normally be covered with a salt bridge layer which is a source for a constant concentration of the measured ion species. This salt bridge serves as an ion bridge between an analyte-containing solution and an ionophoric layer and consists of a small amount of appropriate electrolyte dissolved in a water-permeable hydrophilic polymer.

Suitable hydrophilic polymers include polyvinyl alcohol (PVA), polyethylene oxides, polyethylene oxide ethers, and various polysaccharides. Among the many polysaccharides suitable for this purpose are natural gums such as agar and agarose, cellulose and cellulose derivatives such as cellulose esters, cellulose ethers and benzyl cellulose. The hydrophilic polymer must be chosen to have at least moderate dimensional stability in the presence of, and be substantially insoluble in, liquid analyte at ambient temperatures.

To protect the salt bridge layer, it is covered with an inert substantially water-impermeable layer such as Silastic ® or PVC. By and large, the covering for the salt bridge can be made from any impervious hydrophobic polymer, such as the oleophilic polymers mentioned hereinabove for use as matrix in forming the dispersed carbon layer.

Only a small edge surface of the salt bridge layer is exposed to provide a restricted area in contact with an analyte by which migration of salt between the salt bridge layer and the analyte is minimized, while at the same time providing an ionic bridge between the sensor and reference cells when analyte is placed between them. When the salt bridge layer is properly formulated so that the electrolyte concentration therein remains substantially constant, the reference signal therefrom also remains constant.

The salt bridge material is readily formulated by dissolving an electrolyte in an hydrophilic polymer. This formulation can easily be screen-printed onto an appropriate substrate and solidified by heating and/or drying, depending upon the particular type of hydrophilic polymer which is used. In the case of PVA, drying alone may be sufficient. However, in other instances, it may be desirable to include in the formulation a small amount of a cross-linking agent and an appropriate initiation system which can be activated by heating the printed layer to a moderate temperature, e.g., 50° C.

D. Conductive Material

Generally, a wide variety of conductive materials can be used in the invention half cells so long as the interface with the dispersed carbon layer has a stable conductor contact potential difference and is free from oxidation. Though noble matals such as silver and gold are often preferred as the conductive material, because of their chemical inertness, base metals such as copper, nickel, iron, tin, cadmium and aluminum can also be used, because they are not subject to stringent oxidative conditions in the device of the invention.

In all cases, the conductive layer(s) of the half cells of the invention must be provided with terminations by which the electrode can be connected to an electrometer-amplifier to measure any potential difference between the half cells. These terminations may merely be an extension of the conductive layer or they may be made by specially printing a contiguous conductive layer of either the same or a different conductive metal. The precise method of termination is not critical and will largely be determined by fabrication economics for any given performance level.

It is, of course, necessary that the conductor pattern which is not in contact with the dispersed carbon layer be shielded from analyte liquid by a layer which is both electrically insulating and chemically inert with respect to the analyte liquid. This is normally done by covering the nonchemically functional portion of the conductor pattern with a layer of chemically inert insulating material such as a polymer or glass. The polymers which are suitable for the matrix of the membrane and carbon layers are also in general suitable as an insulator for those portions of the conductive layer which need to be shielded.

E. Fabrication

The electrode half cell of the invention and the sensors made therefrom have a further advantage in that they can be fabricated in very small sizes and as very thin layers. As is apparent from the drawing, the half cell of the invention is essentially a simple multilayer laminate, i.e., it is a stack of thin layers or films. A particularly convenient method of forming the layers is to screen print them on whatever substrate is used. For example, in the case of the conductive material, a dispersion of finely divided particles of the conductive material in an inert organic medium is formed, screen-printed in the desired pattern onto the insulating substrate and fired to sinter the conductive material and form a "continuous" conductive layer.

On the other hand, finely divided particles of the conductive material can be dispersed in a photosensitive medium, coated on the insulating substrate, exposed through an appropriate phototool to harden the dispersion in the desired pattern, and developed to remove the unexposed dispersion.

Likewise, the successive carbon and ionophore layers can be applied by the same techniques or others which will be well known by those skilled in the art.

Of primary importance, however, is the formation of the interdiffusion zone between the carbon and ionophoric layers. The interdiffusion zone must not extend completely through either the ionophoric membrane or the carbon layer. However, the zone must be extensive enough to diffuse any charge gradient developed by the passage of current as required by the electrometer-amplifier used for the measurement. The reason for this is that there must exist zones of substantially pure ionophoric layer and substantially pure conductive layer to effect the transition from electron flow to ion flow in support of the electrical current. The concentration gradient is developed at the sample solution/ionophoric layer interface and extends inwardly toward the interdiffusion zone and a substantially zero concentration gradient should reside at the carbon layer side of the zone. On the other hand, from the carbon layer side of the interdiffusion zone, the carbon layer provides a conductive path for electrons and also allows the transport of ions at the interface to support current flow by the electrometer-amplifier.

Though in theory these criteria might be met by a large number of separate stacked layers, each having appropriate changes in concentration of ionophore and carbion particles, this would be very onerous and very expensive. A much easier way to accomplish this is to plasticize both of the matrix polymers whereupon the laminated layers will autogenically interdiffuse due to mutual solubilization. In addition, interdiffusion of the layers, either with or without plasticization, can be effected by the application of pressure and/or by the application of heat for a time sufficient to effect the proper degree of interdiffusion.

However, by whatever method the interdiffusion zone is formed, it is essential that the interdiffusion zone have a high-to-low dielectric gradient from the membrane to the carbon layer. In addition, it is essential that the interdiffused zone be stable. For this last reason, it is very desirable to incorporate a cross-linking agent in the binder component of either or both of the polymer matrices to effect both physical and chemical stabilization of both the membrane and carbon layers as well as the interposed interdiffusion layer.

The following procedure is typical of the way in which the electrode half cells of the invention and sensors made therefrom are fabricated in layers using screen-printing techniques.

The various layers are built up on a planar substrate which typically has dimensions $1'' \times 2'' \times 0.025''$ ($2.5 \times 5.0 \times 0.006$ cm). The resultant structure is commonly referred to as a chip. The substrate must be chemically inert with respect to analyte and the layers placed thereon. It must also be dimensionally stable and immiscible with respect to the analyte and/or overlying layers. The dimensions, however, are not critical and may be varied. The composition of the substrate is chosen on the basis of cost, ease of manufacture, and durability. Although for the purposes of this discussion ceramic is chosen as the substrate, other substrates, for example, Mylar ® polyester film, can be employed.

The first or bottommost functional layer of the device is the conductor, usually silver. A silver paste is screened over a ceramic substrate using a 250 mesh screen and allowed to dry for 5 to 10 minutes at room temperature. It is then dried for an additional 10 minutes at 150° C. and finally fired for 30 minutes at 850° C.

The second functional layer of the device is the insulator, usually glass, which is printed over the conductor pattern using a 165 mesh screen in such manner that the conductor paths are protected, but the contact area of the electrode is exposed. It is dried for approximately 5 minutes at room temperature and for an additional 10 minutes at 150° C. Finally, it is fired for 30 minutes at 850° C. If a polymeric substrate is used then the same function can be served by use of a dielectric photosensitive polymer system (e.g., a dry film photoresist) to form the appropriate protective pattern.

The third functional layer of the device, the carbon layer, is printed above the conductor pattern. A 165 mesh screen is employed. The carbon layer is dried for approximately 5 minutes at room temperature and cured for another 20 minutes at 160° C.

The fourth layer of the device, the polyvinylchloride (PVC)/ionophore layer, is printed above the carbon pattern using a 165 mesh screen. The composition of this layer is variable, depending on the species to be detected.

The PVC typically has an inherent viscosity of about 0.65 and comprises about 11.3 weight percent of the formulation. The ionophore comprises about 1.1 weight percent of the formulation and imparts ion-selectivity to the device. Various plasticizers can also be present. The PVC/ionophore is dried for about 10 minutes at room temperature and then cured for 30 minutes at 35° C.

The choice of ionophore varies depending on the electrolyte to be detected. For example, valinomycin is selective for potassium; methylmonensin for sodium; and nonactin for ammonium.

Using the materials described above, it was not necessary to carry out any special procedures to form the interdiffusion zone at the interface of the ionophoric and carbon layers. The reason for this was that in both layers the same plasticizer and same polymer were used, which gives to the layers a substantial degree of mutual solubility which, without further manipulation, results in formation and stabilization of the zone within a very short time after fabrication. Because the interdiffusion zone can be formed so easily by this method, it is a preferred way of fabricating this segment of the electrode half cells of the invention. The extent and rate of interdiffusion can be adjusted by increasing or decreasing the mutual solubility of the layers, e.g., by changing the composition and/or concentration of the plasticizer in either or both layers.

In most instances it will be preferred that the layered electrode half cell of the invention be combined on the same substrate with a similar half cell which is coated with a salt bridge layer, which layer in the presence of analyte serves as an ionic bridge between the two half cells. The primary purpose of this second half cell is to be a source of a constant signal, i.e., a constant potential, based upon a fixed concentration of electrolyte.

A PVA/salt bridge layer is printed on the reference electrode side of the sensor, above the PVC layer, using a 165 mesh screen. Typically, the PVA (polyvinyl alcohol) formulation consists of approximately 37 weight percent PVA; 0.17 weight percent Triton ®-x 100 nonionic surfactant; 0.75 weight percent Foamaster TM DP-122 NS. Where the analyte is an electrolyte, for example, potassium, the PVA layer is doped with a standard amount of that electrolyte, for example, KCl.

The above-described PVA layer is dried for 10 minutes at room temperature and cured for 30 minutes at 35° C.

The topmost layer of the sensor is an overcoat layer, typically of silicon rubber, which is printed with a 165 mesh screen over the reference side of the sensor. It is dried for 10 minutes at room temperature and cured for 1 hour at 50° C. in a humidified $CO_2$ atmosphere. This topmost layer covers the entire chip except for a small area which is left open to provide electrical contact between analyte solution contained in the receiving zone (described below) and the PVA/salt layer. The primary purpose of the small open area is to allow electrical contact between the analyte solution and the salt bridge while minimizing contamination and concentration changes within the salt bridge layer arising from such contact. Within the time frame of most measurements (usually less than five minutes), no significant migration of analyte into the salt bridge layer will take place and thus signal drift from this source is, for all practical purposes, eliminated.

In the operation of sensors made from the electrode half cells of the invention, the liquid electrolytic analyte is placed in on area overlapping the two half cells atop an appropriate insulating layer. The analyte must overlap the half cells sufficiently to establish ionic contact with both half cells. This area between the half cells constitutes a receiving zone for the analyte. Though it is not required, this zone may be given a dish-shaped or other type of configuration to define the zone and hold the liquid analyte in place more effectively. In addition, the zone can be provided with an inert adsorbent material to hold the analyte more tightly within the receiving zone.

FIELDS OF USE

The device of this invention is useful in measuring concentrations of a large number of analytes of clinical interest in biological samples. (By analyte is meant a substance whose concentration is desired to be determined.) The biological sample can be a biological fluids such as whole blood, blood serum, blood plasma, saliva, cerebrospinal fluid, or urine or it can be a cell or tissue extract. The analyte is often an electrolyte (e.g., $H+$, $Na+$, $Ca^{2+}$, $K+$, $Cl-$, $NH_4+$, $HCO_3-$, etc.), gas (e.g., $CO_2$, $O_2$), or a metabolite (e.g., glucose, blood urea nitrogen, triglycerides, phenylalanine, tyrosine, creatinine, etc.) present in one of these biological fluids. Other analytes include proteins, drugs, hormones, vitamins, enzymes, enzyme substrates, antibodies, polysaccharides, bacteria, protozoa, fungi, viruses, cell and tissue antigens and other blood cell or blood fluid substances.

Electrolytes are measured potentiometrically by the device of this invention. By potentiometric measurement is meant that the potential difference between the half cells is measured at substantially zero current flow (less than $1 \times 10^{-12}$ and preferably less than about $1 \times 10^{-15}$ amperes).

An ion-selective membrane is used in the device to select the ion for the ultimate potentiometric measurement. In the case of the electrolytes, an ionophore is used to select the desired ion for measurement. Table 1 above lists typical ionophores and the analyte for which they are selective.

Metabolities, enzymes and enzyme substrates are usually measured by devices which couple the selectivity inherent in enzyme-substrate reactions with that of the ion-selective sensor. The ultimate detection is a potentiometric measurement of the resultant ion (such as a blood urea nitrogen (BUN) measurement through the urease-coupled generation of $NH_4+$). Table 3 below lists some of the analytes which can be measured through enzyme-coupled sensors and also gives the species which is measured.

TABLE 3

| ENZYME-COUPLED MEASUREMENT DEVICES | | |
|---|---|---|
| Analyte | Substrate/Enzyme | Species Monitored |
| BUN | Urease | $NH_4+$ |
| Creatinine | Creatininase | $NH_4+$ |
| Lactic acid | Lactic dehydrogenase | $NAD+$ |
| Triglycerides | Lipase | $H+$ |
| Cholinesterase | Acetylcholine | $H+$ |

The device of this invention can also be used in the measurement of analytes in immunochemical-coupled assays. For example, an antigen can be measured by using a urease-labelled antibody to the antigen in the detector. The detector is sensitive to the amount of $NH_4+$ generated by the urease, which in turn is related to the amount of antigen in the biological fluid. Thus, various antigens or antibodies of clinical interest can be measured through this type of device. Other enzyme labels, such as decarboxylase, or hydrolase, or electroactive labels, such as porphyrins, quinones, ferrocene, or $NAD+$, can be used in the immunochemical coupled device. The selectivity in these devices is due primarily to the specific binding of antigen and antibody.

Besides the previously discussed applications in clinical or diagnostic chemistry, the device of this invention can also be used in the detection of analytes of interest in, for example, chemical procedures, manufacturing processes, chemical hazard detection (dosimeters), and microbial growth processes.

DETAILED DESCRIPTION OF THE DRAWING

FIG. 1 is a schematic overhead view of a typical sensor which incorporates two of the half cells of the invention as the indicator and reference sides of the sensor. Visible in this view of the device are ceramic substrate 1 over which are printed conductor leads 3 and 3' which underlie indicator half cell 4 and reference half cell 4', both of which are multilayered structures as described with respect to FIG. 2 below. In operation, conductor leads 3 and 3' are connected electrically to an electrometeramplifier.

Figure 2:
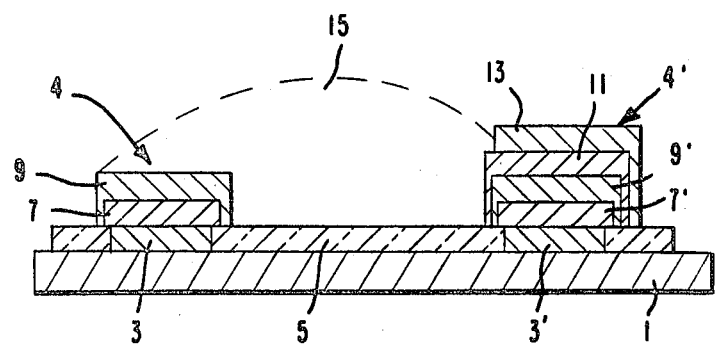

FIG. 2 is a schematic sectional view of the analytical electrode of FIG. 1 taken along the vertical section defined by lines A—A.

Two-layered half cells are shown which are printed upon a common ceramic substrate 1 made from 96% by weight alumina. The layered electrode half cell on the left 4 is the indicator half cell and the layered electrode half cell on the right 4' is the reference half cell.

The lowermost layer of the indicator or sensing half cell 4 consists of a patterned area of silver metal 3 which serves as an electrical conductor to which leads of an electrometer are attached. Likewise, the lowermost layer of the reference half cell 4' has a functionally identical silver metal layer 3'. To insulate the two conductive layers 3 and 3' when the device is contacted with analyte 15, a layer of dielectric (insulating) material 5 is interposed between the sides of the silver layers 3 and 3'. A dispersed carbon layer 7 and 7' is positioned upon the conductor layers 3 and 3' in such manner that the layers are physically shielded from any direct contact with the analyte 15. As shown here, the overlying carbon layers 7 and 7' each overlap slightly the insulating layer 5 to effect complete shielding of the conductors 3 and 3'.

Upon the carbon layers are positioned ionophoric layers 9 and 9' in such manner that the carbon layer is also physically shielded from any direct contact with analyte 15.

Up to this point the structures of half cells 4 and 4' are functionally the same and structurally similar except for possible differences in geometry.

However, the ionophoric layer 9' of reference half cell 4' is overlaid by salt bridge layer 11 and covered by a protective layer 13 which physically shields reference half cell 4' from direct contact with analyte 15. The salt bridge layer 11 is substantially but incompletely covered by impermeable layer 13 in such manner that the exposure of the salt bridge layer 11 to the liquid analyte 15 is quite restricted relative to the total surface of the layer.

Layer 11 comprises a constant composition of electrolyte to which layer 9' is sensitive and selective. Protective layer 13 ensures that the electrolyte composition is not altered during the measurement (e.g. ~2 minutes) and hence functions to maintain a constant E.M.F. during measurement of analyte. The exposed edge of layer 11 ensures contact of the reference half cell with the analyte, while at the same time retarding ionic migration into the bulk of layer 11.

The invention will be better understood by reference to the following examples in which the fabrication and operation of the half cells of the invention are described in detail.

EXAMPLES

Example 1

A potassium sensor chip was fabricated using the procedure described hereinabove. In particular, the sensor consisted of a 1"×2"×0.025" (2.5×5.0×0.06 cm) alumina chip upon which were printed two terminated silver conductor patterns. The entire uncoated area of the substrate chip was covered with a layer of glass to shield the sides of the conductor pattern from analyte. Correspondingly, the sides of the dispersed carbon layer were shielded by the overlying ionophoric layer. In the reference electrode half cell, the ionophoric layer was shielded from the analyte by the overlying salt bridge layer. However, the salt bridge layer was covered with a layer of Silastic ® polymer film except for one side of the ion-selective membrane which was left exposed to provide for limited ionic contact with the analyte.

The compositions of the carbon, ionophoric and salt bridge layers are given in Table 4 which follows:

TABLE 4

| Composition of Electrode Functional Layers | |
|---|---|
| | % wt. |
| Carbon Dispersion Layer | |
| Electrodac-423 SS (Acheson Colloids CO., Port Huron, MI) which comprises: | |
| Vinyl chloride/vinyl acetate copolymer | |
| 2-Butoxyethylacetate | |
| Carbon | |
| Ionophoric Layer | |
| Poly(vinyl chloride) | 11.3 |
| Dioctyl adipate (DOA) | 26.9 |
| Cyclohexanone | 60.7 |
| Valinomycin | 1.1 |
| | 100.0 |
| Salt Bridge Layer | |
| Poly(vinyl alcohol) | 37.4 |
| Water | 60.1 |
| KCl | 1.3 |
| Triton ® X-100 | 0.1 |
| Foamaster ™ DP-122NS | 1.1 |
| | 100.0 |

Example 2

The sensor chip of Example 1 was then used to determine the potential difference between two aqueous analytes, one consisting of 1 mMol of KCl and 140 mMol of NaCl and the other consisting of 10 mMol of KCl and 140 mMoles of NaCl.

Figure 3:
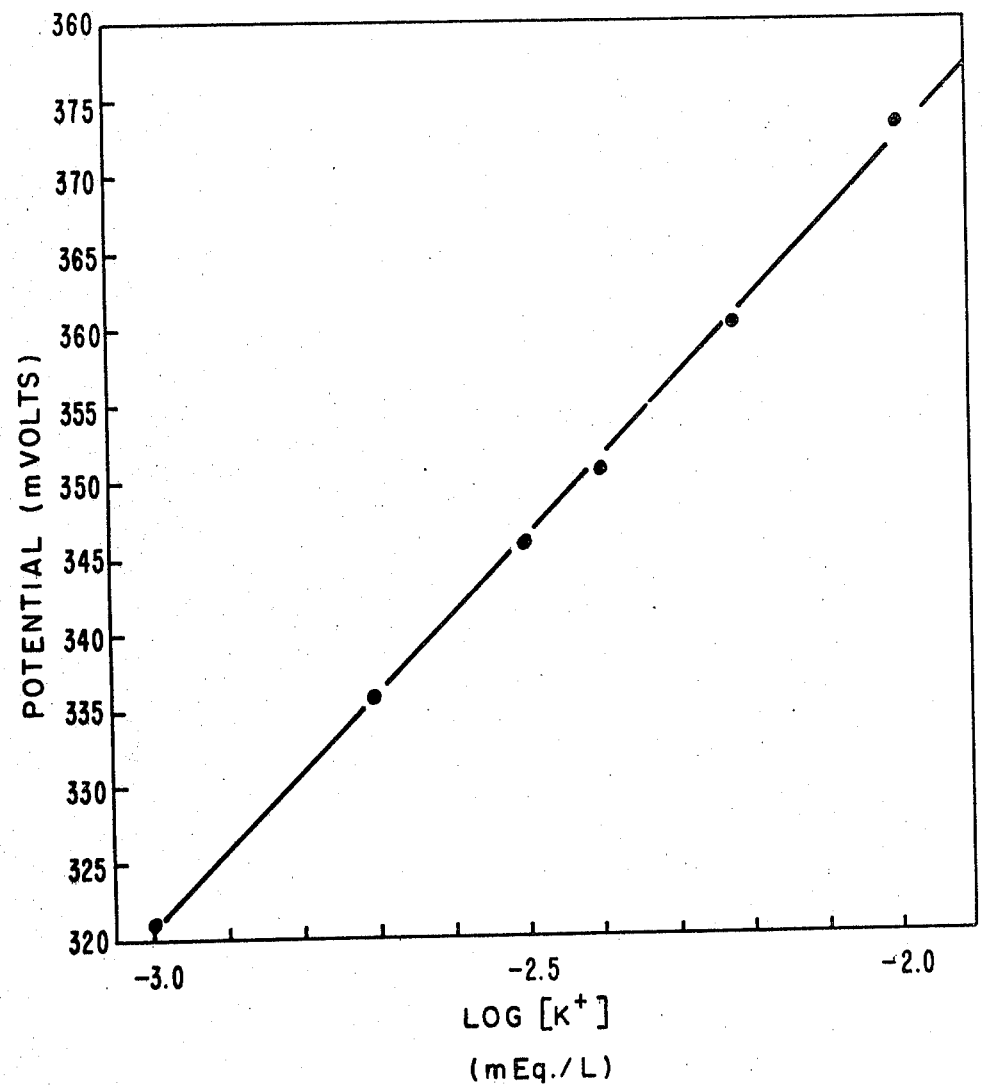
FIG. 3 is a response curve for a sensor made in accordance with the invention.

In this test, the sensor was first exposed to the weaker KCl analyte solution and then, after 60 seconds, the weak electrolyte was rapidly washed off and replaced with the more concentrated KCl analyte solution and the cycle was repeated two times, during which the potentiometric voltage was continuously recorded. A plot of the correlation of potential (mVolts) as a function of time reveals that a full response to each 10-fold change in K+ concentration took place in less than 10 seconds with a slope (or sensitivity) of at least 56 mV. As used herein, the term full response refers to attainment of at least 99% of steady state. Sensitivity is determined by the relationship mV/pK+. The response curve for this electrode (signal voltage vs. K+ concentration) is given in FIG. 3.

In addition, upon observing the response for 10 minutes, it was found that the drift was below 1 mV/min. Furthermore, upon observing the individual response of the sensors it was found that the reference half cell was, as it should be, essentially nonresponsive to the analyte. That is, it gave an essentially constant signal during that extended period.

Examples 3-10

A series of eight sensor chips was fabricated in the above-described manner in which the ion-selective membrane contained 3% by weight valinomycin and the amount of DOA plasticizer was varied from zero to 90% by weight, the weight ratio of ionophore to PVC binder in each formulation being constant. Using the same $K^+$-containing analytes as in Example 1, the sensitivity of each sensor was determined by measuring the slope of its response curve. The results were as follows:

TABLE 5
Effect of Plasticizer Level in the Ionophoric Layer Upon Sensitivity

| Example No. | Amount of Plasticizer, % wt. | Slope ($\Delta$mV/pK +) mV |
|---|---|---|
| 3 | 0 | Noisy, unstable |
| 4 | 25 | Noisy, unstable |
| 5 | 40 | Noisy, unstable |
| 6 | 50 | 52 |
| 7 | 60 | 58 |
| 8 | 70 | 56 |
| 9 | 80 | 57 |
| 10 | 90 | 53 |

The above data show that for this particular polymer system (0.65 I.V. PVC), in excess of 40% by weight plasticizer was necessary to obtain suitable ion carrier mobility through the ionophoric layer.

Examples 11-14

Four additional chip sensors were fabricated in the manner of Example 1. In each a different solvent system for the ionophoric layer was used. Again using the same potassium-containing analytes as in Example 1, the sensitivity of each of the sensors was measured by determining the slope of its response curve. The results were as follows:

TABLE 6
Effect of Solvent Composition of Ionophoric Layer on Sensitivity

| Example No. | Solvent Composition | Slope ($\Delta$mV/pK +) mV |
|---|---|---|
| 11 | Cyclohexanone | ca. 57 |
| 12 | N—methyl-pyrrolidone | ca. 59 |
| 13 | Isophorone | ca. 45 |
| 14 | Tetrahydrofuran | ca. 57 |

The above data show that the solvent medium used in casting the ionophoric layer can have a significant effect on sensitivity of the sensor. The data suggest that, for any given binder/ionophore system, the solvent can be chosen to improve sensitivity to a small but significant degree.

Examples 15-25

Another series of sensor chips was formulated in the manner of Example 1 in which the thickness of the ionophoric layer was varied to determine the effect of membrane thickness upon sensitivity of the chip. For a still further comparison, an electrode was formulated and tested which contained no ionophoric membrane at all. Each of these chips was evaluated as in the previous example for sensitivity by measurement of the slope of the response curve. The results given in Table 7 below are the average obtained from tests of 2 or 3 electrode chips at each thickness level.

TABLE 7
Effect of Ionophoric Layer Thickness on Sensitivity

| Example No. | Ionophoric Layer Thickness (mils) | Slope ($\Delta$mV/pK +) mV |
|---|---|---|
| 15 | — | 14 |
| 16 | 0.05 | 34 |
| 17 | 0.08 | 55 |
| 18 | 0.15 | 44 |
| 19 | 0.2 | 54 |
| 20 | 0.4 | 54 |
| 21 | 0.5 | 54 |
| 22 | 0.7 | 54 |
| 23 | 1.1 | 54 |
| 24 | 2.7 | 53 |
| 25 | 6.0 | 40 |

The foregoing data show that an ionophoric membrane thickness of at least about 0.2 mil is needed for this particular matrix/plasticizer system. It is likely that the poorer sensitivity of the relatively thin layers was due to unevenness and pinholes which occur in such thin films. On the other hand, it is apparent that the sensitivity decreases to an unsatisfactory level when the ionophoric layer thickness exceeds about four or five mils. This latter adverse effect is probably due at least in part to the fact that the signal impedance is reduced excessively with such high ionophoric layer thickness. An ionophoric membrane thickness of no more than 3.0 mil is preferred.

Examples 26-32

A still further series of sensor chips was fabricated in the manner of Example 1, but the amount of ionophore in the ion-selective layer was varied to determine the effect of ionophore concentration on the sensitivity of the chips. The sensitivity of each of these chips was measured as in the previous examples by determining the slope of the response curve. The results in Table 8 are the average of 2 or 3 chips of each composition.

TABLE 8
Effect of Ionophore Concentration on Sensitivity

| Example No. | Ionophoric Concentration % wt. | Slope ($\Delta$mV/pK +) mV |
|---|---|---|
| 26 | 0.1 | 52 |
| 27 | 0.3 | 58 |
| 78 | 0.5 | 61 |
| 29 | 1.0 | 60 |
| 30 | 2.0 | 64 |
| 31 | 3.0 | 61 |
| 32 | 5.0 | 60 |

These data show that quite good sensitivity can be obtained at even very low ionophore concentrations, but that maximum sensitivities are attained at an ionophore level of at least about 0.5% by weight. Furthermore, there seems to be no additional advantage to using ionophore concentrations above 2-3% by weight since no greater sensitivity is obtained. Though for this analyte good sensitivities were obtained at low ionophore concentrations, other more concentrated ionic analytes will likely require higher ionophore levels to get a satisfactory sensitivity of 50 mV or higher.

I claim:

1. A sensor for the potentiometric measurement of an ion in a liquid sample, comprising:
   a dimensionally stable, chemically inert, electrically insulating, substantially planar substrate layer having disposed thereon a sensing half-cell and a reference half-cell, the sensing half-cell comprising:
  (a) a terminated layer of electroconductive material in intimate contact with the substrate layer, the electroconductivity being at least $1 \times 10^2$ $(ohm \cdot cm)^{-1}$, the electroconductive material layer having coated thereon
  (b) a carbon layer of finely divided particles of carbon uniformly dispersed in a matrix of organic polymeric binder having coated thereon
  (c) an ion-selective membrane layer comprising an ionophoric material dispersed in a matrix of dielectric organic polymer, the layer having an electrical impedance at least two orders of magnitude greater than the impedance of the carbon layer, the interface between the ion-selective membrane layer and the dispersed carbon layer comprising a zone in which the layers are partially interdiffused, layers (a) and (b) being shielded from both chemical and electroconductive contact with the liquid sample;

the reference half-cell comprising:
  (a) a terminated layer of electroconductive material in intimate contact with the substrate layer, the electroconductivity being at least $1 \times 10^2$ $(ohm \cdot cm)^{-1}$, the electroconductive material layer having coated thereon
  (b) a carbon layer of finely divided particles of carbon uniformly dispersed in a matrix of organic polymeric binder having coated thereon
  (c) an ion-selective membrane layer comprising an ionophoric material dispersed in a matrix of dielectric organic polymer, the layer having an electrical impedance at least two orders of magnitude greater than the impedance of the carbon layer, the interface between the ion-selective membrane layer and the dispersed carbon layer comprising a zone in which the layers are partially interdiffused, layers (a) and (b) being shielded from both chemical and electroconductive sample, the ion-selective membrane having coated thereon
  (d) a salt bridge layer comprising a predetermined concentration of an ion capable of interacting with the ionophoric material, the ion being dissolved in a solid hydrophilic polymer, the salt bridge layer being substantially, but incompletely, shielded from ionic contact with the liquid sample by an overlying layer of an inert liquid-impermeable electrically insulating layer to define a shielded and an unshielded surface area of the salt bridge layer.

the sensing half-cell and the reference half-cell being spaced apart on the substrate layer to define a liquid sample receiving zone adapted to allow the liquid sample to make ionic contact with both the ion-selective membrane layer of the sensing half-cell and the unshielded surface area of the salt bridge layer of the reference half-cell, such that application of the liquid sample to the sensor does not substantially change the predetermined ion concentration in the salt bridge layer of the reference half-cell thereby establishing a stable reference potential.

2. The sensor of claim 1 wherein the ion-selective membrane layer comprises polyvinyl chloride.

3. The sensor of claim 2 wherein the ion-selective membrane layer further comprises a plasticizer.

4. The sensor of claim 3 wherein the plasticizer is dioctyl adipate.

5. The sensor of claim 1 wherein the carbon layer comprises vinyl chloride/vinyl acetate copolymer.

6. The sensor of claim 5 wherein the carbon layer further comprises a plasticizer.

7. The sensor of claim 6 wherein the plasticizer is dioctyl adipate.

8. The sensor of claim 1 wherein the electroconductive material is silver.

9. The sensor of claim 1 wherein the ionophoric material is valinomycin.

10. The sensor of claim 1 wherein the ion-selective membrane layer and the carbon layer are both comprised of plasticized polyvinyl chloride.

11. A method of making a multi-laminate electrode half-cell of the type defined in claim 1, comprising:
  (a) preparing a substantially planar substrate layer,
  (b) screen-printing on the substrate layer a thin layer of a paste of electroconductive material in a pattern which defines a conductive path and a contact area,
  (c) screen-printing an insulator layer over the conductive path, leaving the contact area exposed,
  (d) screen-printing a carbon layer over the contact area of the electroconductive material, and
  (e) screen-printing an ion-selective membrane over the carbon layer.

12. A method for measuring the concentration of an ion contained in a liquid sample comprising (1) placing a quantity of sample in the receiving zone of the sensor of claim 1 by which an ion transport path is completed between the ion-selective membrane layer of the sensing half-cell and the salt bridge layer of the reference half-cell, and (2) measuring the potential between the conductive layers of the half-cells at a current flow of less than $1 \times 10^{-12}$ amperes.

13. A reference half-cell to be used in conjunction with a sensing half-cell for the potentiometric measurement of an ion in a liquid sample, comprising a dimensionally stable, chemically inert, electrically insulating substrate layer having coated thereon
  (a) a terminated layer of electroconductive material in intimate contact with the substrate layer, the electroconductivity being at least $1 \times 10^2$ $(ohm \cdot cm)^{-1}$, the electroconductive material layer having coated thereon;
  (b) a carbon layer of finely divided particles of carbon uniformly dispersed in a matrix of organic polymeric binder having coated thereon
  (c) an ion-selective membrane layer comprising an ionophoric material dispersed in a matrix of dielectric organic polymer, the layer having an electrical impedance at least two orders of magnitude greater than the impedance of the carbon layer, the interface between the ion-selective membrane layer and the dispersed carbon layer comprising a zone in which the layers are partially interdiffused, layers (a) and (b) being shielded from both chemical and electroconductive sample, the ion-selective membrane having coated thereon
  (d) a salt bridge layer comprising a predetermined concentration of an ion capable of interacting with the ionophoric material, the ion being dissolved in a solid hydrophilic polymer, the salt bridge layer being substantially, but incompletely, shielded from ionic contact with the liquid sample by an overlying layer of an inert liquid-impermeable electrically insulating layer to define a shielded and an unshielded surface area of the salt bridge layer;

such that application of the liquid sample to the reference half-cell does not substantially change the predetermined ion concentration in the salt bridge layer, thereby establishing a stable reference potential.

14. The sensor of claim 13 wherein the ion-selective membrane layer comprises polyvinyl chloride.

15. The sensor of claim 14 wherein the ion-selective membrane layer further comprises a plasticizer.

16. The sensor of claim 15 wherein the plasticizer is dioctyl adipate.

17. The sensor of claim 13 wherein the carbon layer comprises vinyl chloride/vinyl acetate copolymer.

18. The sensor of claim 17 wherein the carbon layer further comprises a plasticizer.

19. The sensor of claim 18 wherein the plasticizer is dioctyl adipate.

20. The sensor of claim 13 wherein the electroconductive material is silver.

21. The sensor of claim 13 wherein the ionophoric material is valinomycin.

22. The reference half-cell of claim 13 wherein the salt bridge layer comprises polyvinyl alcohol.

* * * * *